United States Patent
Choi et al.

(10) Patent No.: US 11,826,458 B2
(45) Date of Patent: Nov. 28, 2023

(54) GINGER WATER COMPOSITION HAVING GINGER EXTRACT AND METHOD FOR MANUFACTURING THE SAME

(71) Applicant: HANAMOA Co., Ltd., Seoul (KR)

(72) Inventors: Yoon Jeong Choi, Seoul (KR); Eil Sup Yoon, Seoul (KR)

(73) Assignee: HANAMOA CO., LTD., Seoul (KR)

( * ) Notice: Subject to any disclaimer, the term of this patent is extended or adjusted under 35 U.S.C. 154(b) by 0 days.

(21) Appl. No.: 17/928,181

(22) PCT Filed: May 20, 2021

(86) PCT No.: PCT/KR2021/006258
§ 371 (c)(1),
(2) Date: Nov. 28, 2022

(87) PCT Pub. No.: WO2021/241934
PCT Pub. Date: Dec. 2, 2021

(65) Prior Publication Data
US 2023/0190634 A1    Jun. 22, 2023

(30) Foreign Application Priority Data

May 28, 2020    (KR) .......................... 10-2020-0064092

(51) Int. Cl.
*A61K 8/9794*    (2017.01)
*A61Q 19/02*    (2006.01)

(52) U.S. Cl.
CPC ............ *A61K 8/9794* (2017.08); *A61Q 19/02* (2013.01)

(58) Field of Classification Search
CPC ..................................................... A61K 8/9794
See application file for complete search history.

(56) References Cited

FOREIGN PATENT DOCUMENTS

| | | | | |
|---|---|---|---|---|
| EP | 2193785 A2 | * | 6/2010 | ............... A23L 2/52 |
| JP | 2003-048845 A | | 2/2003 | |
| KR | 10-2011-0033690 A | | 3/2011 | |
| KR | 10-2019-0037966 A | | 4/2019 | |
| KR | 20190131884 A | * | 11/2019 | |
| KR | 10-2020-0017699 A | | 2/2020 | |
| KR | 10-2176033 B1 | | 11/2020 | |

OTHER PUBLICATIONS

Supardan et al., "Solvent extraction of ginger oleoresin using ultrasound", Makara, Sains, vol. 15, No. Nov. 2, 2011: 163-167. (Year: 2011).*

* cited by examiner

*Primary Examiner* — Gina C Justice
(74) *Attorney, Agent, or Firm* — Bridgeway IP Law Group, PLLC; Sang Ho Lee; Hyun Woo Shin

(57) ABSTRACT

A method of preparing a ginger water composition containing a ginger extract according to one embodiment of the present invention includes obtaining a ginger extract from a ginger root; mixing an organic solvent with the ginger extract; providing ultrasonic waves and obtaining a first solution; mixing water with the first solution; supplying heat and obtaining a second solution; and filtering the second solution.

2 Claims, 3 Drawing Sheets

| | HEAT EXTRACTION | ULTRASONIC EXTRACTION, 30M | ULTRASONIC EXTRACTION, 90M |
|---|---|---|---|
| BRIGHTNESS | 62.27 | 61.16 | 75.03 |
| YELLOWNESS | 66.98 | 68.40 | 74.30 |
| SAMPLE IMAGE |  |  |  |

GINGER WATER COMPOSITION HAVING GINGER EXTRACT AND METHOD FOR MANUFACTURING THE SAME

FIELD OF THE INVENTION

The present invention relates to a ginger water composition containing a ginger extract and a method of preparing the same.

BACKGROUND ART

Ginger (*Zingiber officinale*) is widely used as a spice that enhances the taste of food and a medical substance that cannot be omitted from oriental medicine prescriptions. Particularly, ginger contains aromatic substances, which is essential oil ingredients, such as borneol, cineole, citral, phenol and alkaloid, such that bad odors and tastes such as fishy odors are removed and central nausea is stopped, and spicy ingredients such as gingerol and shogaol, which are known to have a strong sterilizing effect against bacteria such as Typhus and Cholera.

Human skin color is essentially determined by the number of melanin cells, that is, melanocytes, the concentration of melanin and the degree of melanin biosynthesis, and greatly affected by congenital factors such as personal genetic factors, and external factors such as the intensity of UV rays and the number of exposures. The more the melanin pigment, the darker the skin and the stronger the resistance to UV rays. Blacks have hundreds of times the amount of melanin pigment in their skin compared to whites, and thus the outward color of the skin is very dark.

When the melamine-forming melanocytes in human skin are not evenly distributed for any reason, pigment spots are created, making them brighter or darker than the surrounding areas of the skin. In order to solve this problem, a whitening agent that makes such pigment spots at least partially uniform is used. Many skin whitening agents contain a somewhat potent tyrosinase inhibitor, and as these skin whitening agents, mainly, hydroquinones, for example, hydroquinone derivatives such as arbutin, vitamin C, for example, ascorbic acid derivatives such as ascorbyl palmitate, kojic acid, for example, kojic acid derivatives such as kojic acid dipalmitate are used as particularly commercially useful skin and hair whitening agents.

Vitamin C and ascorbic acid derivatives do not act directly as a tyrosinase inhibitor, so the whitening effect is insufficient, and kojic acid may cause skin allergies. For these reasons, a whitening cosmetic composition containing a medical plant extract, which does not cause skin troubles or allergies is being studied.

The inventors studied a ginger water composition containing a ginger extract among plant extracts and a method of preparing the same for a long time, and after trial and error, have reached the completion of the present invention.

SUMMARY OF THE INVENTION

TECHNICAL PROBLEM

The present invention is directed to providing a ginger water composition containing a ginger extract with an economically reliable whitening effect from a readily available plant and a method of preparing the same.

Other unspecified objects of the present invention will be additionally considered within the range that can be easily deduced from the following detailed description and effects thereof.

TECHNICAL SOLUTION

According to one aspect of the present invention, a method of preparing a ginger water composition containing a ginger extract, which includes: obtaining a ginger extract from a ginger root; mixing an organic solvent with the ginger extract; providing ultrasonic waves and obtaining a first solution; mixing water with the first solution; supplying heat and obtaining a second solution;

and filtering the second solution, is provided.

The organic solvent may include at least one of butylene glycol and hexanediol.

Ultrasonic waves at a frequency of 20 to 30 kHz may be provided for 1 to 2 hours.

*In the step of obtaining a second solution, the second solution may be obtained under a temperature condition of 60 to 70° C.

In the step of filtering the second solution, the second solution may be sequentially filtered through multiple filters with different pore sizes.

After the step of obtaining a first solution, a quality control step for controlling at least one of the solubility, odor and microbial content of the first solution may be further included.

According to another aspect of the present invention, a ginger water composition containing a ginger extract prepared according to the above-described preparation method is provided.

According to still another aspect of the present invention, a ginger water composition containing a ginger extract, which includes 0.1 to 1.2 wt % of a ginger extract, 4.5 to 7.5 wt % of butylene glycol and 2 wt % of hexanediol with respect to the total weight of the composition, is provided.

ADVANTAGEOUS EFFECTS

According to one embodiment of the present invention, a ginger water composition that can exhibit a whitening effect and a wrinkle-improving effect can be obtained.

Meanwhile, it should be added that even if not specified herein, effects disclosed herein and potential effects thereof, which are expected by the technical features of the present invention, are treated as being described herein.

The accompanying drawings are exemplified by reference for understanding the technical idea of the present invention, and the scope of the present invention is not limited thereto.

DETAILED DESCRIPTION OF EXEMPLARY EMBODIMENTS

To describe the present invention, when detailed description of the related art is determined to unnecessarily obscure the subject matter of the present invention, the detailed description will be omitted.

The terms used herein are used only to describe specific examples, not to limit the present invention. Singular expressions include plural referents unless the context clearly indicates otherwise. The terms "include" and "have" used herein designate the presence of characteristics, numbers, steps, actions, components or members described in the specification or a combination thereof, and it should be understood that the possibility of the presence or addition of one or more other characteristics, numbers, steps, actions, components, members or a combination thereof is not excluded in advance.

Hereinafter, a ginger water composition containing a ginger extract according to the present invention and a method of preparing the same will be described in detail with reference to the accompanying drawings, and in the description with reference to the accompanying drawings, the same reference numbers will be assigned to the same or corresponding elements, and the overlapping descriptions thereof will be omitted.

Figure 1:
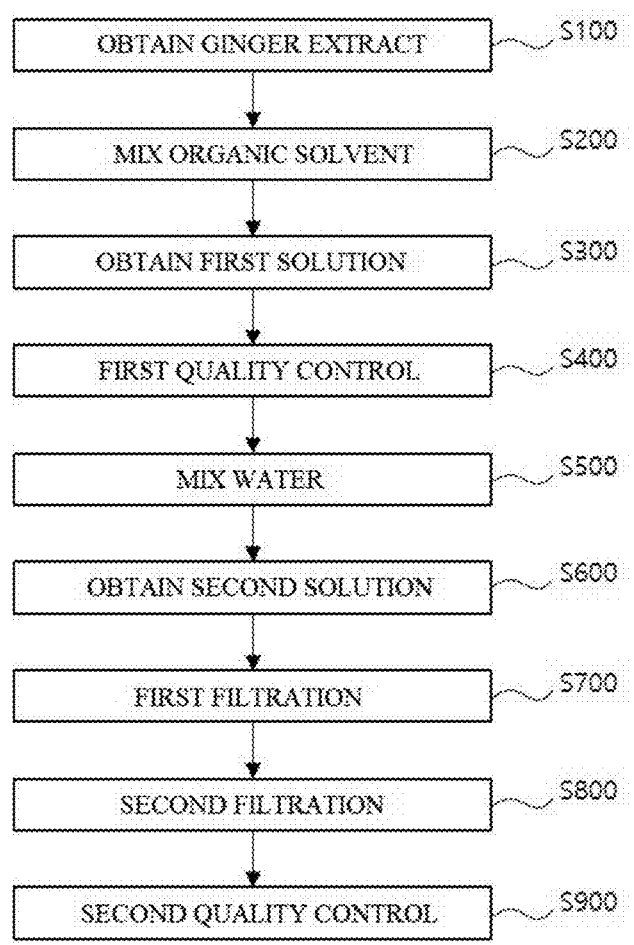
FIG. 1 is a flow chart illustrating a method of preparing a ginger water composition containing a ginger extract according to the present invention.

FIG. 1 is a flow chart illustrating a method of preparing a ginger water composition containing a ginger extract according to the present invention. Ginger water is prepared through the preparation method of FIG. 1.

Referring to FIG. 1, the method may include a step of obtaining a ginger extract (S100), a step of mixing an organic solvent (S200), a step of obtaining a first solution (S300), a step of mixing water (S500), a step of obtaining a second solution (S600), and filtering steps (S700, S800), and further include quality control steps (S400, S900).

The step of obtaining a ginger extract (S100) is a step of obtaining a ginger extract from a ginger root. The step of obtaining a ginger extract may include steaming, drying and extracting steps.

The steaming step is a step of steaming the ginger root. As an apparatus used in the steaming step, any apparatus that can steam ginger, which is a raw material, that is, cook ginger with hot steam, can be used. For example, the steaming step may be carried out by putting ginger on a commonly used steaming grill for dumplings, and steaming the ginger in an autoclave under constant temperature and pressure.

The steaming step may be performed at 100 to 140° C., and preferably 115 to 130° C. for minutes to 1 hour, and preferably, 20 to 50 minutes.

The drying step is a step of drying the steamed ginger. The drying step may be performed at 40 to 80° C., and preferably 50 to 70° C. for 10 to 30 hours, and preferably 12 to 24 hours, and the steaming step and the drying step may be repeated 6 or 7 times.

The extracting step is a step of performing extraction using a water-soluble organic solvent or water. As an organic solvent, a lower alcohol such as methanol, ethanol or isopropanol, and a solvent such as acetone or dioxane may be used alone or in combination.

The ginger extract obtained by the above-described method is a ginger concentrate, and may be in a state of a viscous solution (emulsion).

The ginger extract according to the present invention has a whitening function. The whitening function of a cosmetic may be verified by a tyrosinase inhibitory effect thereof. The ginger extract contained in ginger water in the present invention exhibits a tyrosinase inhibitory effect.

Figure 3:
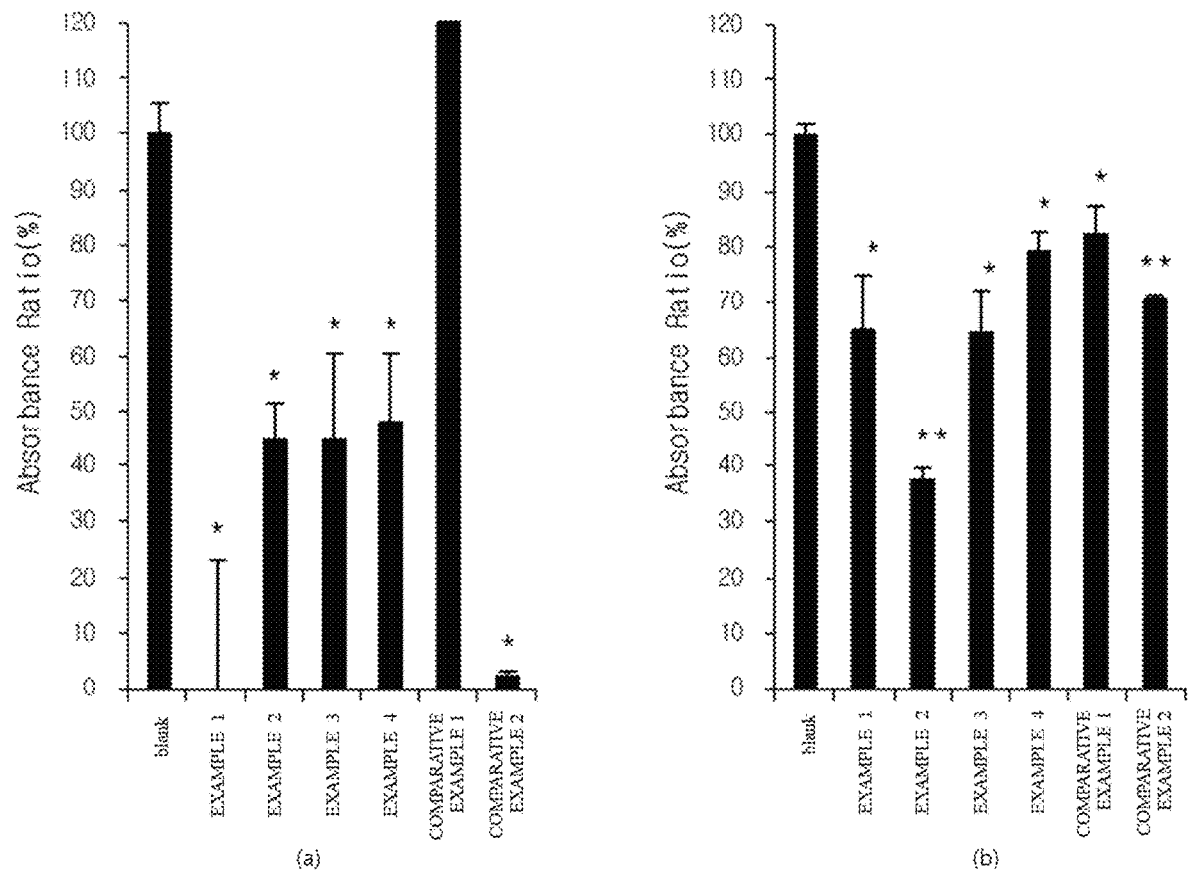
FIG. 3 shows the results of experiments for verifying the whitening effect of a ginger extract.

FIG. 3 shows the results of experiments for verifying the whitening effect of the ginger extract obtained by steaming, drying and extracting ginger according to examples (the cases of repeating steaming and drying 6, 7, 8 and 9 times correspond to Examples 1, 2, 3 and 4, respectively), wherein a Rhodosporidium babjevae strain-derived extract was used as Comparative Example 1, and arbutin widely known as a material having a whitening effect was used as Comparative Example 2.

The degree of tyrosinase activity is measured, a smaller value represents a better whitening effect. In addition, in the drawing, * indicates that the error range is within 5% ($p<0.05$), and ** indicates that the error range is within 0.1% ($p<0.001$).

FIG. 3A is a result of the measurement of the activity of tyrosinase by treating a sample with tyrosine, and FIG. 3B is a result of the measurement of the activity of tyrosinase by treating DOPA.

Referring to FIGS. 3A and 3B, in all examples, the activity of tyrosinase was confirmed, and particularly, in Examples 1 and 2, a higher whitening effect was confirmed, compared to arbutin (Comparative Example 2).

As described above, the ginger extract according to the present invention has a whitening function, and both ginger water containing a ginger extract and a cosmetic based on ginger water can exhibit a whitening function.

Referring to FIG. 1 again, the step of mixing an organic solvent (S200) is a step of mixing an organic solvent with the ginger extract. The organic solvent may include at least one of butylene glycol and hexanediol.

Butylene glycol may be added to improve the compatibility of a ginger extract. The ginger extract may be mixed with water or an oil preparation to finally be a ginger water composition, and butylene glycol may be added to uniformly mix the ginger extract with water or the oil preparation.

Hexanediol may be 1,2-hexanediol, which may impart a preserving and antisepsis function to the ginger water.

The step of obtaining a first solution (S300) is a step of providing ultrasonic waves to the mixture of the ginger extract and an organic solvent, and thereby obtaining a first solution.

In the step of obtaining a first solution (S300), ultrasonic waves at a frequency of 20 to 30 kHz may be provided. In addition, the ultrasonic waves may be provided for 1 to 2 hours. For example, the ultrasonic waves may be provided for 1.5 hours.

Since the ginger concentrate has a high Brix degree (Brix %), an extraction method using ultrasonic waves is suitable. The extraction using ultrasonic waves may improve low turbidity, stability and solubility, compared to a heat extraction method (not using ultrasonic waves).

Figure 2:
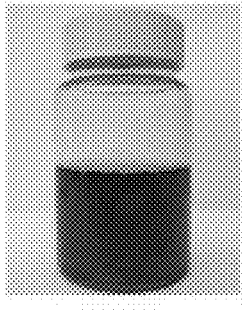
FIG. 2 is an image of an extracted first solution.
Figure 2:
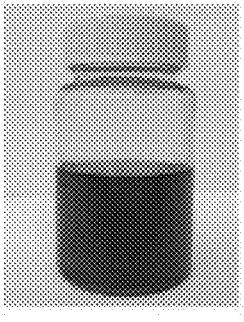
Figure 2:
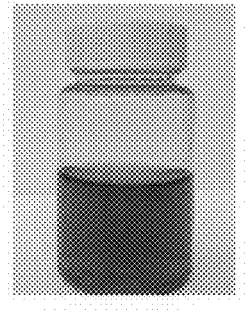

FIG. 2 is an image of the extracted first solution. Referring to FIG. 2, the brightness and yellowness of the first solution obtained by the ultrasonic extraction method were further improved compared to a heat extraction method.

In addition, in the case of ultrasonic extraction by providing ultrasonic waves for 1.5 hours, it can be seen that the brightness and yellowness are remarkably improved.

The ginger extract and the organic solvent may be contained in a container. A vibrator coupled to the container, or a vibrator immersed in the mixture of the ginger extract and the organic solvent may generate ultrasonic waves. The ginger extract and the organic solvent may be finely degraded by the ultrasonic waves. The first solution may be stably obtained using the ultrasonic waves. Meanwhile, the mixture in the container may be stirred with a stirrer in the container as needed when the ultrasonic waves are provided.

The first solution may be extracted from the mixture of the ginger extract and the organic solvent after the ultrasonic application is terminated. For example, the first solution may be obtained from the remainder excluding suspended matter and/or precipitate in the mixture of the ginger extract and the organic solvent after the ultrasonic application is terminated.

The first quality control step (S400) is a step of controlling at least one of the solubility, microbial content and odor of the first solution. The solubility may be controlled by a temperature or stirring. The microbial content may be controlled by removing microbes contained in the first solution.

The odor (off-flavor) control may be controlled by a separate process for reducing the peculiar odor of ginger. Particularly, the odor (off-flavor) control may be carried out by a method of stirring after adding activated carbon to the first solution. The added activated carbon may be used in an amount of 0.1 wt % with respect to the total weight of the first solution, but the present invention is not limited thereto.

There are multiple pores in the activated carbon, and an odor may be controlled (removed) by adsorbing a substance generating a odor into a pore of the activated carbon.

The step of mixing water (S500) is a step of mixing water with the first solution. Here, water may be distilled water.

The step of obtaining a second solution (S600) is a step of providing heat to the mixture of the first solution and water, thereby obtaining a second solution. The step of obtaining a second solution (S600) may be sequentially or simultaneously performed with the step of mixing water with the first solution (S500).

The second solution may be obtained at 60 to 70° C. That is, the mixture of the first solution and water may be heated to 60 to 70° C., thereby obtaining a second solution.

The first solution and water may be contained in a container. Heat may be supplied to the container, and a heat source is not limited. Due to the heat supply, the temperature of the first solution and water may be maintained at 60 to 70° C. When the temperature is maintained at 60 to 70° C., solubility may be improved without a chemical modification of the mixture of the first solution and water.

Meanwhile, a heat supply time may be 1 to 2 hours. That is, heat may be supplied for 1 to 2 hours while the temperature of the mixture of the first solution and water is maintained at 60 to 70° C. For example, heat supply may be performed for 1.5 hours.

A second solution may be extracted from the mixture of the first solution and water during or after heat supply. For example, the second solution may be obtained from the remainder excluding suspended matter and/or precipitate in the mixture of the first solution and water.

The filtering steps (S700, S800) are steps of filtering the second solution. In the filtering steps, the second solution may be sequentially filtered through multiple filters with different pore sizes. That is, the second solution may be filtered several times, and the pore size of the filter used in filtration may vary according to the number of filtrations. The pore size of the filter may be smaller as the number of filtrations increases.

The filtering steps may include first filtration (S700) using a filter having a pore size of 0.8 μm; and second filtration (S800) using a filter having a pore size of 0.2 μm. Filtration efficiency may be gradually improved by filtration with an increasingly fine filter.

Meanwhile, in the filtering steps (S700, S800), the activated carbon that has been added for odor control may be also filtered.

Finally, the second quality control step (S900) may be performed, and is a step of controlling at least one of the solubility, microbial content and odor of a product obtained through filtration. That is, the solubility, microbial content and odor of the product obtained through filtration may be measured, and when they are inappropriate, quality may be managed in the same manner as in the first quality control step (S400).

The product determined to be suitable in the second quality control step may be finally obtained as "ginger water." The ginger water obtained according to the present invention may be a raw material of a cosmetic such as a toner, lotion, cream or serum. The cosmetic produced based on the ginger water may exhibit a whitening function.

The ginger water composition obtained according to the present invention may include to 1.2 wt % of the ginger extract, 4.5 to 7.5 wt % of butylene glycol (butanediol) and 1.5 to 2.5 wt % of hexanediol with respect to the total weight of the composition. Here, the butylene glycol may be 1,3-butylene glycol, and the hexanediol may be 1,2-hexanediol.

When the content of the ginger extract is less than 0.1 wt %, it is difficult to expect the whitening effect due to the ginger extract, and when the content of the ginger extract is more than 1.2 wt %, due to the ginger odor, the extract may cause discomfort to the user.

In addition, the ginger water composition obtained according to the present invention may include 88.8 to 93.9 wt % of distilled water, 0.1 to 1.2 wt % of the ginger extract, 4.5 to 7.5 wt % of butylene glycol and 1.5 to 2.5 wt % of hexanediol. Here, the butylene glycol may be 1,3-butylene glycol, and the hexanediol may be 1,2-hexanediol.

Specifically, the ginger water composition obtained according to the present invention may include 0.2 wt % of the ginger extract, 7 wt % of butylene glycol and 2 wt % of hexanediol with respect to the total weight of the composition. Moreover, the ginger water composition may include 90.8 wt % of distilled water, 0.2 wt % of the ginger extract, 7 wt % of butylene glycol and 2 wt % of hexanediol.

The ginger water containing 0.2 wt % of the ginger extract may be used in a cosmetic containing a large amount of moisture, such as a toner.

In addition, the ginger water composition obtained according to the present invention may include 1 wt % of the ginger extract, 5 wt % of butylene glycol (butylene glycol) and 2 wt % of hexanediol with respect to the total weight of the composition. Moreover, the ginger water composition may include 92 wt % of distilled water, 1 wt % of the ginger extract, 5 wt % of butylene glycol and 2 wt % of hexanediol.

The ginger water containing 1 wt % of the ginger extract may be used in a high-viscosity cosmetic such as a serum.

In addition, the ginger water composition obtained according to the present invention may have a specific gravity of 0.980 to 1.020, a pH of 4.5 to 7.5, and a refractive index of 1.320 to 1.360. For example, the specific gravity may be 1, the pH may be 6.48, and the refractive index may be 1.340.

The above-described ginger water may be a raw material for a cosmetic. Cosmetics using ginger water may include a toner, a skin, a lotion, a cream, a serum, and an essence. Other than these, the ginger water may be provided for various cosmetics such as a color cosmetic, soap, a body shampoo, a hand soap, a shampoo and a rinse (hair conditioner), and the type of cosmetic is not limited.

The scope of protection of the present invention is not limited to the description and expression of the embodiments explicitly described above. In addition, it should also be stated that the scope of protection of the present invention may not be limited due to obvious changes or substitutions in the technical field to which the present invention belongs.

The invention claimed is:

1. A method of preparing a ginger water composition containing a ginger extract, comprising:
obtaining a ginger extract from a ginger root;
mixing an organic solvent with the ginger extract;
providing ultrasonic waves and obtaining a first solution;
performing first quality control for controlling the solubility, odor and microbial content of the first solution;
mixing water with the first solution;
supplying heat and obtaining a second solution;
filtering the second solution; and
performing second quality control for controlling the solubility, odor and microbial content of the second solution,
wherein the organic solvent includes butylene glycol and hexanediol,
in the step of obtaining a first solution,
ultrasonic waves at a frequency of 20 to 30 kHz are provided to the mixture of the ginger extract and the organic solvent for 1.5 hours,
in the first quality control step, odor is controlled by adding 0.1 wt % of activated carbon with respect to the entire first solution and stirring the mixture,
in the step of obtaining a second solution,
the mixture of the first solution and the ginger water is heated for 1.5 hours, thereby obtaining the second solution under a temperature condition of 60 to 70° C., and
in the step of filtering a second solution,
the second solution is filtered through a first filter with a pore size of 0.8 μm, and then a second filter with a pore size of 0.2 μm.

2. A ginger water composition, which is prepared by the preparation method of claim 1, and comprises 0.1 to 1.2 wt % of the ginger extract, 4.5 to 7.5 wt % of butylene glycol and 2 wt % of hexanediol with respect to the total weight of the composition.

* * * * *